(12) United States Patent
Taylor

(10) Patent No.: US 8,022,018 B2
(45) Date of Patent: Sep. 20, 2011

(54) QUATERNIZED DITHIAZINES AND METHOD OF USING SAME IN TREATMENT OF WELLS

(75) Inventor: Grahame Nigel Taylor, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 12/862,582

(22) Filed: Aug. 24, 2010

(65) Prior Publication Data

US 2011/0152131 A1   Jun. 23, 2011

Related U.S. Application Data

(63) Continuation-in-part of application No. 12/643,521, filed on Dec. 21, 2009.

(51) Int. Cl.
| | |
|---|---|
| C23F 11/10 | (2006.01) |
| C23F 11/08 | (2006.01) |
| C07D 279/04 | (2006.01) |
| C11D 3/28 | (2006.01) |
| E21B 43/16 | (2006.01) |

(52) U.S. Cl. ............ 507/247; 166/242.4; 166/305.1; 166/307; 405/211.1; 422/7; 422/12; 507/242; 507/243; 507/252; 507/256; 507/258; 510/401; 510/402; 544/53; 544/83; 544/180; 546/304; 546/347; 585/950

(58) Field of Classification Search ............ 507/247, 507/242, 243, 252, 256, 257, 258; 166/242.4, 166/305.1, 307; 405/211.1; 422/7, 12; 510/401, 510/402; 544/53, 83, 180; 546/304, 347; 585/950
See application file for complete search history.

(56) References Cited

U.S. PATENT DOCUMENTS

| | | | |
|---|---|---|---|
| 4,271,132 A | 6/1981 | Eickmeyer | |
| 4,452,764 A | 6/1984 | Oakes et al. | |
| 4,491,527 A * | 1/1985 | Lange et al. | 508/272 |
| 4,569,766 A | 2/1986 | Kool et al. | |
| 5,074,991 A | 12/1991 | Weers | |
| 5,128,049 A | 7/1992 | Gatlin | |
| 5,376,749 A | 12/1994 | Miller et al. | |
| 5,413,627 A | 5/1995 | Landeck et al. | |
| 5,462,721 A | 10/1995 | Pounds et al. | |
| 5,478,541 A | 12/1995 | Samuels et al. | |
| 5,674,377 A | 10/1997 | Sullivan, III et al. | |
| 6,063,346 A | 5/2000 | Luna | |
| 6,180,057 B1 | 1/2001 | Taylor et al. | |
| 6,267,938 B1 | 7/2001 | Warrender et al. | |
| 6,582,624 B2 | 6/2003 | Titley et al. | |
| 6,663,841 B2 | 12/2003 | Salma et al. | |
| 6,964,940 B1 | 11/2005 | Treybig et al. | |
| 7,264,786 B2 | 9/2007 | Pakulski et al. | |

FOREIGN PATENT DOCUMENTS

| | | |
|---|---|---|
| WO | WO 9201481 A1 | 2/1992 |
| WO | WO-2008049188 | 2/2008 |

* cited by examiner

*Primary Examiner* — Timothy J. Kugel
(74) *Attorney, Agent, or Firm* — John Wilson Jones; Jones & Smith, LLP

(57) ABSTRACT

Corrosion of metallic tubulars in an oil, gas or geothermal well may be inhibited by introducing into the well a dithiazine or dithiazine of the formula:

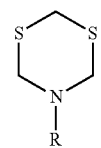

(I)

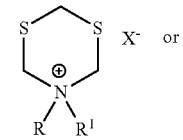

(II)

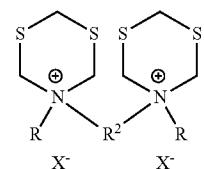

(III)

wherein R is selected from the group consisting of a $C_1$ to $C_{12}$ saturated or unsaturated hydrocarbyl group or a $C_1$ to $C_{10}$ ω-hydroxy saturated or unsaturated hydrocarbyl group; $R^1$ is selected from the group consisting of a $C_1$-$C_{24}$ straight chain or branched alkyl group or a $C_1$-$C_{24}$ arylalkyl; $R^2$ is selected from the group consisting of X-$R^4$-X, $R^4$ being a $C_1$-$C_6$ alkyl group; and X is chlorine, bromine or iodine. The dithiazine may he isolated from a whole spent fluid formed by reaction of hydrogen sulfide and a triazine. Alternately, the whole spent fluid containing the dithiazine may be introduced into the well. The dithiazines of formulae (II) and (III) are quaternized derivatives of the dithiazine of formula (I). In addition, the dithiazine or whole spent fluid or quaternized dithiazine may be formulated with at least one component selected from alkyl, alkylaryl arylalkyl or arylamine quaternary salts; mono or polycyclic aromatic amine salts; imidazoline derivative or a quaternary salt thereof; a mono-, di- or trialkyl or alkylaryl phosphate ester; or a monomeric or oligomeric fatty acid.

32 Claims, 12 Drawing Sheets

QUATERNIZED DITHIAZINES AND METHOD OF USING SAME IN TREATMENT OF WELLS

SPECIFICATION

This application is a continuation-in-part application of U.S. patent application Ser. No. 12/643,521, filed on Dec. 21, 2009.

FIELD OF THE INVENTION

The invention relates to methods of inhibiting corrosion in metallic surfaces during treatment of a well by introducing into the well a dithiazine or a dithiazine derivative.

BACKGROUND OF THE INVENTION

During the production life of an oil or gas well, the production zone within the well is typically subjected to numerous treatments. Corrosion of metallic surfaces, such as downhole tubulars, during such treatments is not uncommon and is evidenced by surface pitting, localized corrosion and loss of metal. Metallic surfaces subject to such corrosion are carbon steels, ferritic alloy steels, and high alloy steels including chrome steels, duplex steels, stainless steels, martensitic alloy steels, austenitic stainless steels, precipitation-hardened stainless steels and high nickel content steels.

Further, aqueous fluids, such as those used in drilling and completion, have a high salt content which causes corrosion. Gases, such as carbon dioxide and hydrogen sulfide, also generate highly acidic environments to which metallic surfaces become exposed. For instance, corrosion effects from brine and hydrogen sulfide are seen in flow lines during the processing of gas streams. The presence of methanol, often added to such streams to prevent the formation of undesirable hydrates, further often increases the corrosion tendencies of metallic surfaces.

Further, naturally occurring and synthetic gases are often conditioned by treatment with absorbing acidic gases, carbon dioxide, hydrogen sulfide and hydrogen cyanide. Degradation of the absorbent and acidic components as well as the generation of by-products (from reaction of the acidic components with the absorbent) results in corrosion of metallic surfaces.

The use of corrosion inhibitors during well treatments to inhibit the rate of corrosion on metal components and to protect wellbore tubular goods is well known. Commercial corrosion inhibitors are usually reaction mixtures or blends that contain at least one component selected from nitrogenous compounds, such as amines, acetylenic alcohols, mutual solvents and/or alcohols, surfactants, heavy oil derivatives and inorganic and/or organic metal salts.

Many conventional corrosion inhibitors used to reduce the rate of acid attack on metallic surfaces and to protect the tubular goods of the wellbore are becoming unacceptable in oilfield treatment processes. For instance, many conventional corrosion inhibitors have become unacceptable due to environmental protections measures that have been undertaken. In some instances, such as in stimulation processes requiring strong acids, high temperatures, long duration jobs and/or special alloys, the cost of corrosion inhibitors may be so high that it becomes a significant portion of total costs.

Efforts have been undertaken to find alternative corrosion inhibitors which are cost effective and which are capable of controlling, reducing or inhibiting corrosion.

SUMMARY OF THE INVENTION

Corrosion of metallic tubulars in a well may be inhibited from forming, by introducing into the well a dithiazine of structural formula (I) or a dithiazine derivative of the structural formula (II) or (III):

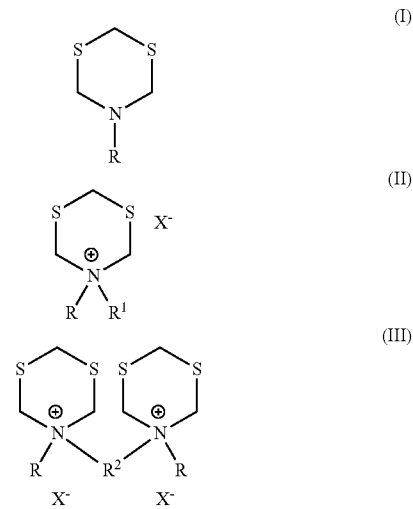

wherein R is selected from the group consisting of a $C_1$ to $C_{12}$ saturated or unsaturated hydrocarbyl group or a $C_1$ to $C_{10}$ ω-hydroxy saturated or unsaturated hydrocarbyl group; $R^1$ is selected from the group consisting of a $C_1$-$C_{24}$ straight or branched chain alkyl group or a $C_1$-$C_{24}$ arylalkyl group; $R^2$ is a straight or branched alkylene group; and X is chlorine, bromine or iodine.

The compound of formula (II) and the compound of formula (III) are quaternized derivatives of the dithiazine of formula (I).

The dithiazine of structure (I) may be isolated from a whole spent fluid formed by reaction of hydrogen sulfide and a triazine, such as 1,3,5-tris(hydroxyethyl)-hexahydro-s-triazine, in a hydrogen sulfide scavenger gas scrubbing operation. Alternately, the whole spent fluid containing the dithiazine of structure (I) may be introduced into the well without isolation of the dithiazine.

Synergistic effects on inhibition of corrosion have further been noted when the isolated dithiazine or whole spent fluid is formulated with at least one component selected from alkyl, alkylaryl or arylamine quaternary salts; mono or polycyclic aromatic amine salts; imidazoline derivatives; a mono-, di-or trialkyl or alkylaryl or arylalkyl phosphate ester; or a monomeric or oligomeric fatty acid. Such components may further be used in combination with the quaternized derivatives of structures (II) and (III).

BRIEF DESCRIPTION OF THE DRAWINGS

In order to more fully understand the drawings referred to in the detailed description of the present invention, a brief description of the drawings is presented, in which.

DETAILED DESCRIPTION OF THE PREFERRED EMBODIMENTS

Figure 1:
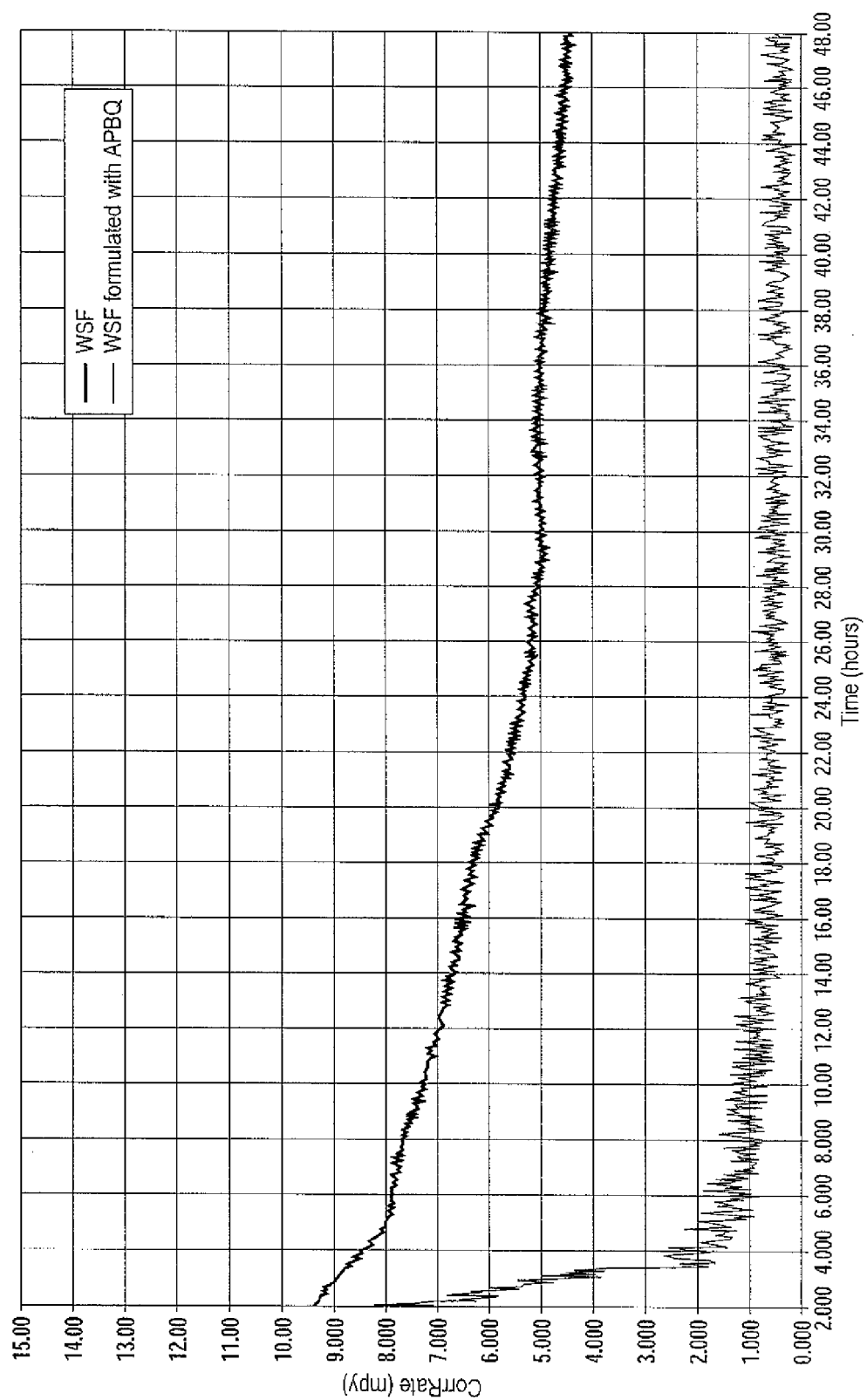
FIGS. 1-7 demonstrate the effectiveness as whole spent fluids (WSF), formulated with additives defined herein.

Corrosion is inhibited during the treatment of a subterranean formation which is petietrated by an oil, gas or geothermal well by introducing into the well a dithiazine of the formula (I):

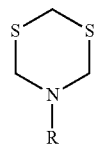
(I)

wherein R is selected from the group consisting of a $C_1$ to $C_{12}$ saturated or unsaturated hydrocarbyl group or a $C_1$ to $C_{10}$ ω-hydroxy saturated or unsaturated hydrocarbyl group; In a preferred embodiment, R is either (i) —$R^3$—OH, wherein $R^3$ is an alkylene group, preferably R is a $C_1$-$C_6$-OH group, most preferably -$CH_2CH_2$-OH; or (ii) a $C_1$-$C_6$ alkyl group, more preferably methyl or ethyl, and most preferably methyl.

The dithiazine of formula (I) is preferably that obtained from the homogeneous fluid which is produced during a hydrogen sulfide scavenger gas scrubbing operation. In such scrubbing operations, a scavenger is introduced to a stream of liquid hydrocarbons or natural gas (sour gas) which contains hydrogen sulfide. In addition, such gas scrubbing operations remove hydrogen sulfide from oil production streams as well as petroleum contained in storage tanks, vessels, pipelines, etc. The scavenger is most commonly a water soluble triazine known in the art. The production of dithiazines during a scrubbing operation using a triazine as scavenger is reported in U.S. Pat. No. 6,582,624. The method disclosed in this patent is reported to dithiazine solid deposits, especially at high operating temperatures, typically greater than 300° C. Typically, dithiazines remain part of the whole spent fluid resulting from the scrubbing operation. Whole spent fluid is typically discarded.

In the method described herein, the dithiazine of formula (I) resulting from the scrubbing operation may be introduced into a gas, oil or geothermal well where it functions as a corrosion inhibitor. The whole spent fluid may be introduced to the well or the dithiazine.

Alternatively, the dithiazine of formula (I) may be isolated from the whole spent fluid by processes known in the art.

In addition to the dithiazines of formula (I), excellent corrosion inhibition properties may be obtained by the use of dithiazine derivatives of either formula (II) or formula (III):

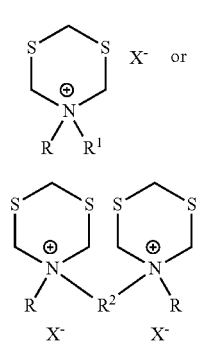

wherein R and X are as described above; $R^1$ is selected from the group consisting of a $C_1$-C24 straight chain or branched alkyl group or a $C_1$-$C_{24}$ arylalkyl group; preferably a $C_1$-C22 alkyl group, more preferably a $C_1$-$C_{12}$ alkyl group, most preferably a $C_1$-$C_6$ alkyl group; $R^2$ is a $C_1$-C6 straight or branched chain alkylene group; and X is chlorine, bromine or iodine. $R^1$ may also be substituted with an aryl group including phenyl and naphthyl. Alternatively, $R^1$ may be a $C_1$-$C_{24}$ arylalkyl group, such as benzyl, wherein the alkyl portion of the arylalkyl group may be linear or branched and the aryl portion of the arylalkyl group may be substituted with a $C_1$-C6 alkyl group, such as methyl. In a preferred embodiment, $R^2$ is -$CH_2$-$CH_2$-$CH_2$-$CH_2$-or -$CH_2$-$CH_2$-$CH_2$-$CH_2$-$CH_2$-. In a preferred embodiment, R of the compounds of formula (ill) is either -$CH_2CH_2$OH or -$CH_3$.

The quaternized product of formula (II) may be prepared by reacting a dithiazine of formula (I) with a halide of the formula $R^1X$ in approximately equimolar ratios. A representative quaternization reaction for the preparation of the compounds of formula (II) may be illustrated as follows:

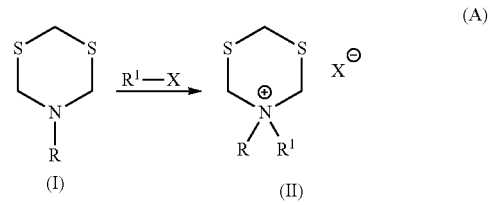

In a preferred embodiment, the $R^1X$ used in the quaternization reaction is benzyl chloride or chloromethyl naphthalene and R is either -$CH_2CH_2$OH or -$CH_3$. Most preferred are those reactants set forth in Table I below which is followed by the designated reaction schemes (B), (C), (D) and (E):

TABLE I

| Reaction Scheme | R | $R^1X$ |
|---|---|---|
| (B) | —$CH_2CH_2$OH | Benzyl chloride |
| (C | —$CH_3$ | Benzyl chloride |
| (D) | —$CH_2CH_2$OH | Chloromethyl naphthalene |
| (E) | —$CH_3$ | Chloromethyl naphthalene |

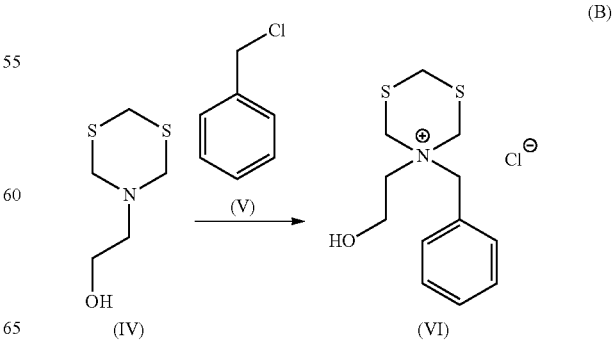

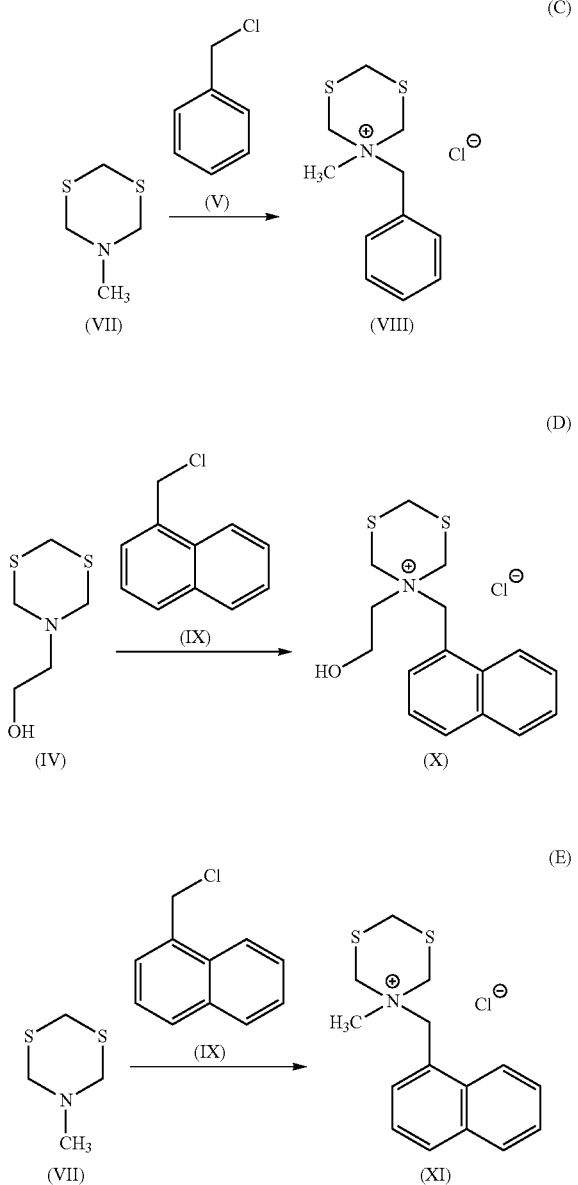

(C)

(D)

(E)

The quaternized product of formula (III) may be prepared by reacting a dithiazine of formula (I) with a dihalide of the formula X-R²-X wherein each R² is a $C_1$-$C_6$ straight or branched alkylene group, preferably -$CH_2$-$CH_2$-$CH_2$-$CH_2$-or -$CH_2$-$CH_2$-$CH_2$-$CH_2$-$CH_2$-; and wherein X is chlorine, bromine or iodine.

A representative quaternization reaction for the preparation of the compounds of formula (III) may be illustrated by reaction scheme (F):

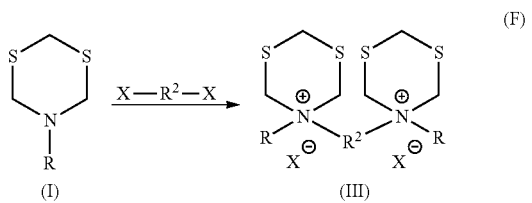

(F)

In a preferred embodiment, the dithiazine of formula (I) (either isolated dithiazine or whole spent fluid) or the quaternized dithiazines of formula (II) and formula (III) may be formulated with at least one other component selected from the groups:

(a) an alkyl, hydroxyalkyl, alkylaryl, arylalkyl or arylamine quaternary salt;

(b) a mono or polycyclic aromatic amine salt;

(c) an imidazoline derivative;

(d) a mono-, di-or trialkyl or alkylaryl phosphate ester; a phosphate ester of hydroxylamines; and phosphate esters of polyols; or (e) a monomeric or oligomeric fatty acid.

In a more preferred embodiment, the dithiazine of formula (I) is formulated with the additive component such that the volume ratio of dithiazine to the additive component is typically between from about 1:0.5 to about 1:2.0, more typically between from about 1:0.8 to about 1:1. Formulating the dithiazine (or quaternized dithiazine) with the additive component may be effectuated by adding the additive to the whole spent fluid or by adding the additive to an alcoholic (for example methanol) solution containing the dithiazine or quaternized dithiazine.

Exemplary of the alkyl, hydroxyalkyl, alkylaryl arylalkyl or arylamine quaternary salts are those alkylaryl, arylalkyl and arylamine quaternary salts of the formula [$N^+R^5R^6R^7R^8$][$X^-$] wherein $R^5$, $R^6$, $R^7$ and $R^8$ contain one to 18 carbon atoms, X is Cl, Br or I. In a preferred embodiment, any or all of the $R^5$, $R^6$, $R^7$ and $R^8$ are a C1-C6 alkyl group or a hydroxyalkyl group wherein the alkyl group is preferably. a $C_1$-$C_6$ alkyl or an alkyl aryl such as benzyl. The mono or polycyclic aromatic amine salt with an alkyl or alkylaryl halide include salts of the formula [$N^+R^5R^6R^7R^8$][$X^-$] wherein $R^5$, $R^6$, $R^7$ and $R^8$ contain one to 18 carbon atoms, X is Cl, Br or I.

Typical quaternary ammonium salts are tetramethyl ammonium chloride, tetraethyl ammonium chloride, tetrapropyl ammonium chloride, tetrabutyl ammonium chloride, tetrahexyl ammonium chloride, tetraoctyl ammonium chloride, benzyltrimethyl ammonium chloride, benzyltriethyl ammonium chloride, phenyltrimethyl ammonium chloride, phenyltriethyl ammonium chloride, cetyl benzyldimethyl ammonium chloride, and hexadecyl trimethyl ammonium chloride. Preferred are alkylamine benzyl quaternary ammonium salts, benzyl triethanolamine quaternary ammonium salts and benzyl dimethylaminoethanolamine quaternary ammonium salts.

In addition, the salt may be a quaternary ammonium or alkyl pyridinium quaternary salt such as those represented by the general formula:

(XII)

wherein $R^9$ is an alkyl group, an aryl group or an alkyl group having from 1 to about 18 carbon atoms and B is chloride, bromide or iodide. Among these compounds are alkyl pyridinium salts and alkyl pyridinium benzyl quats. Exemplary compounds include methyl pyridinium chloride, ethyl pyridinium chloride; propyl pyridinium chloride, butyl pyridinium chloride, octyl pyridinium chloride, decyl pyridinium chloride, lauryl pyridinium chloride, cetyl pyridinium chloride, benzyl pyridinium and an alkyl benzyl pyridinium chloride, preferably wherein the alkyl is a $C_1$-C6 hydrocarbyl group.

The additive may further be an imidazoline derived from a diamine, such as ethylene diamine (EDA), diethylene triamine (DETA), triethylene tetraamine (TETA) etc. and a long chain fatty acid such as tall oil fatty acid (TOFA). Suitable imidazolines include those of formula (IV):

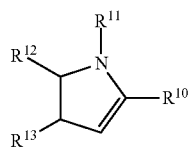

(XIII)

wherein $R^{12}$ and $R^{13}$ are independently a $C_1$-$C_6$ alkyl group more preferably hydrido, $R^{11}$ is hydrido and $R^{10}$ a $C_1$-$C_{20}$ alkyl, a $C_1$-$C_{20}$ alkoxyalkyl group. In a preferred embodiment, $R^{11}$, $R^{12}$ and $R^{13}$ are each hydrido and $R^{10}$ is the alkyl mixture typical in tall oil fatty acid (TOFA).

Suitable mono-, di-and trialkyl as well as alkylaryl phosphate esters and phosphate esters of mono, di, and triethanolamine typically contain between from 1 to about 18 carbon atoms. Preferred mono-, di-and trialkyl phosphate esters, alkylaryl or arylalkyl phosphate esters are those prepared by reacting a $C_{3-18}$ aliphatic alcohol with phosphorous pentoxide. The phosphate intermediate interchanges its ester groups with triethyl phosphate with triethylphosphate producing a more broad distribution of alkyl phosphate esters. Alternatively, the phosphate ester may be made by admixing with an alkyl diester, a mixture of low molecular weight alkyl alcohols or diols. The low molecular weight alkyl alcohols or diols preferably include C6 to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The additive may further be a monomeric or oligomeric fatty acid. Preferred are $C_{14}$-$C_{22}$ saturated and unsaturated fatty acids as well as dimer, trimer and oligomer products obtained by polymerizing one or more of such fatty acids.

The dithiazine or dithiazine derivative may then be introduced as a component of an aqueous treatment fluid into the well. The fluid may be water such as fresh water, brackish water, brine as well as salt-containing water solutions such as sodium chloride, potassium chloride and ammonium chloride solutions.

The amount of dithiazine or quaternized diathiazine introduced into the well is an amount sufficient to inhibit corrosion of the base materials, especially iron, of tubulars in the well. Typically, the amount of dithiazine or quaternized dithiazine introduced into the well is in the range of from about 0.05% to about 5% by volume of the treatment fluid introduced.

Since the dithiazine or quaternized dithiazine dramatically reduces corrosion on metal, it may be used in a variety of industrial applications. Alternatively, the dithiazine or quaternized dithiazine may be introduced prior to or subsequent to, as well as during, a well treatment operation.

Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

The following examples are illustrative of some of the embodiments of the present invention.

All percentages set forth in the Examples are given in terms of weight units except as may otherwise be indicated.

EXAMPLES

Example 1

The following are used to describe components of this Example.

The dithiazine refers to 5-hydroxyethyl-hexahydro-1,3,5-dithiazine of the formula I wherein R is —$CH_2CH_2$—OH.

Unspent fluid ("UF") refers to the hexahydro-1,3,5-tri(hydroxyethyl)-s-triazine of the formula II above wherein each R is —$CH_2CH_2$—OH prior to any spending with hydrogen sulfide.

Whole spent fluid ("WSF") refers to the homogeneous fluid produced in a hydrogen sulfide scavenger gas scrubbing operation wherein the tower was charged with a triazine [1,3,5-tris(hydroxyethyl)-hexahydro-s-triazine] containing fluid in water and methanol. The fluid contains a high level of the dithiazine, it still being in the WSF.

Isolated dithiazine ("iDTZ") refers to dithiazine from the WSF that has been separated out of solution in its pure form.

Formulated products were paired using one of the following additives:
Methyl/Ethylpyridinium benzyl quat (APBQ);
Benzyldimethylcocoamine benzyl quat (ABQ);
TOFA DETA Imidazoline derivative ("TDID");
Benzyl triethanolaminium quat (BTEAQ); and
Benzyl dimethylaminoethanolaminium quat (BDMAEQ).
Formulated WSF refers to the product formed by dissolving the additive in the WSF at a concentration of 12.2 weight percent with methanol at 10 weight percent.

Formulated iDTZ refers to the product prepared by dissolving iDTZ in methanol at a concentration of 9.6 weight percent and then adding to the resultant the additive at a concentration of 19.2 weight percent. This product was then mixed for a brief period while heating to approximately 60° C.

Figure 2:
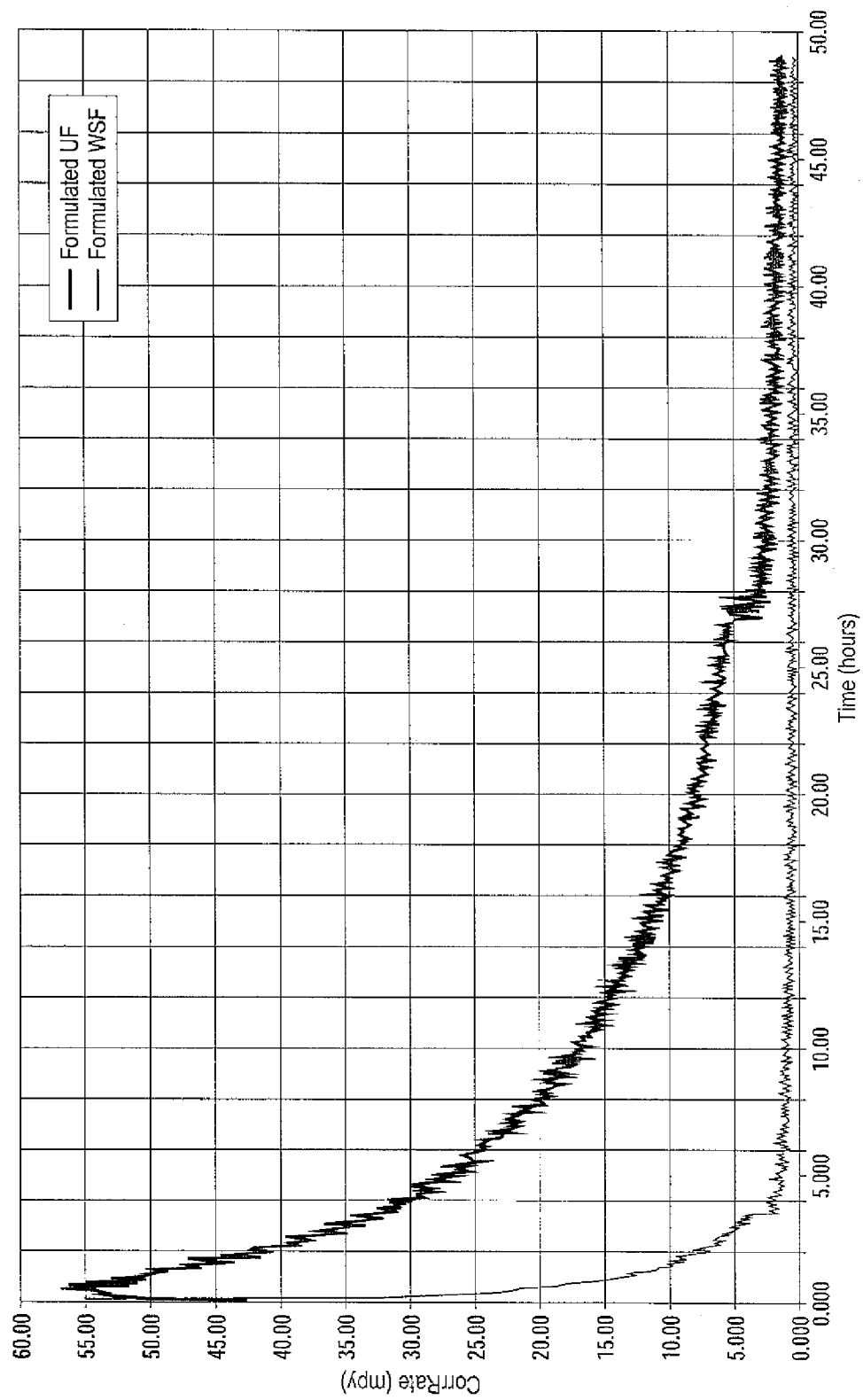
Figure 3:
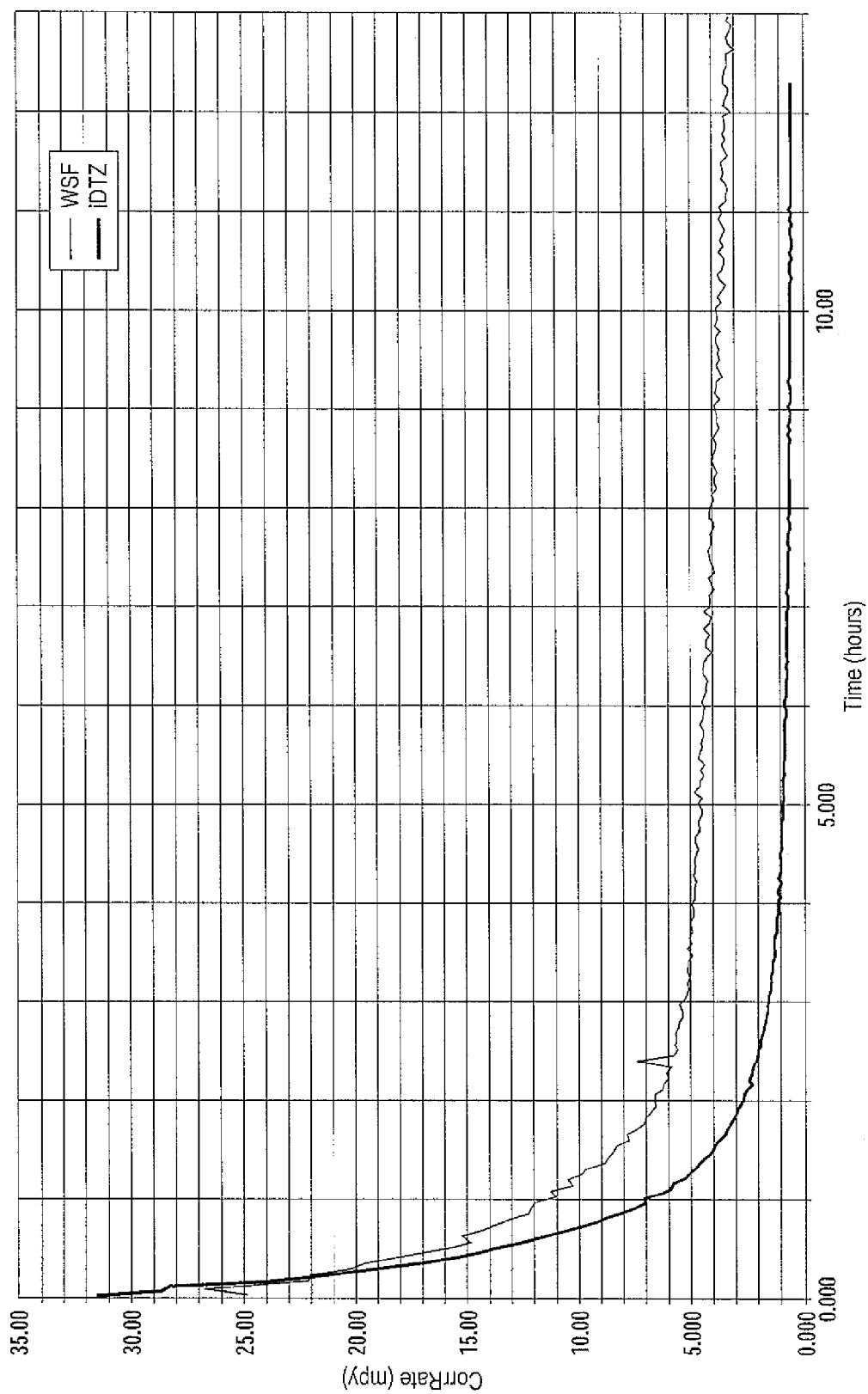
Figure 4:
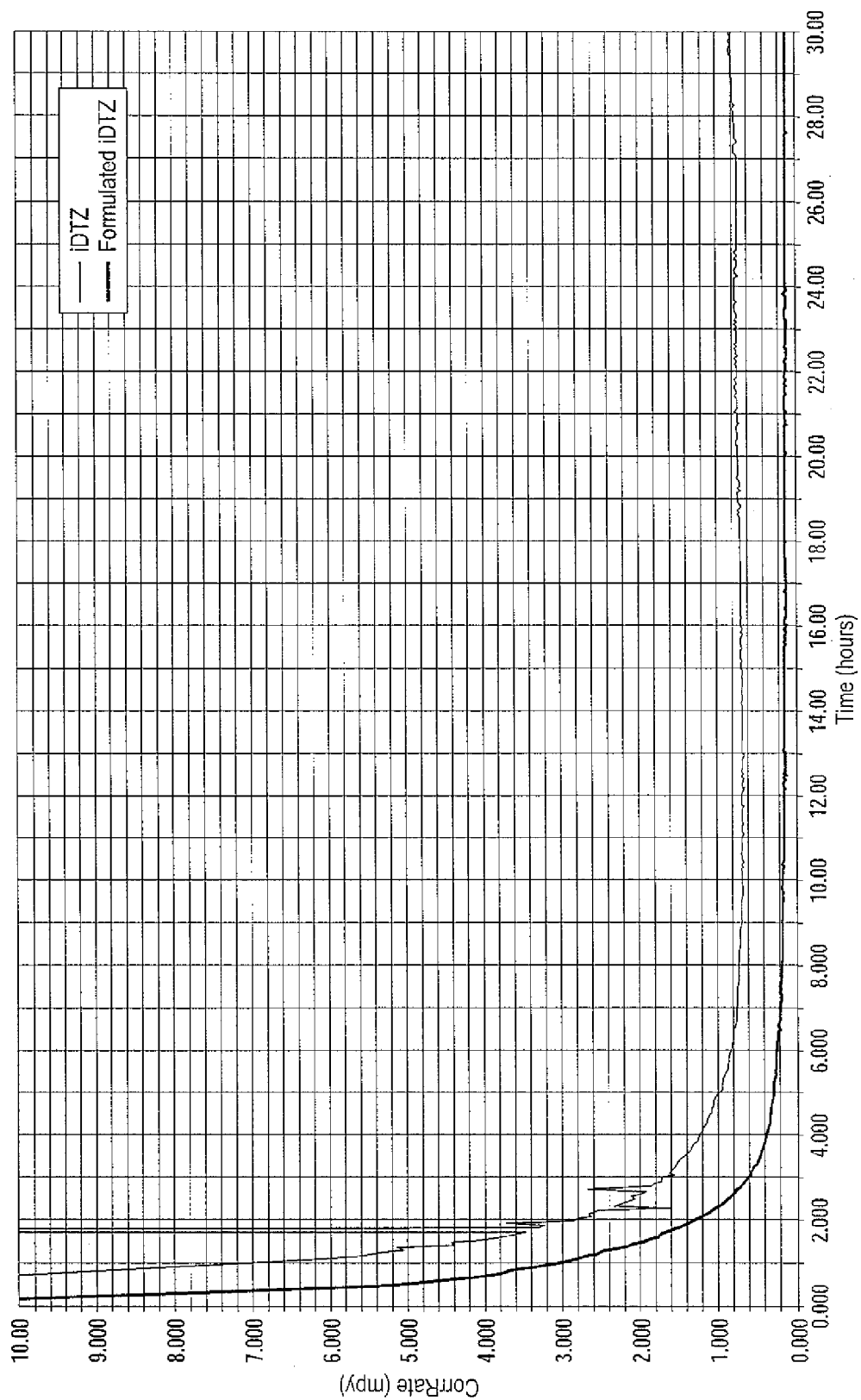
Figure 5:
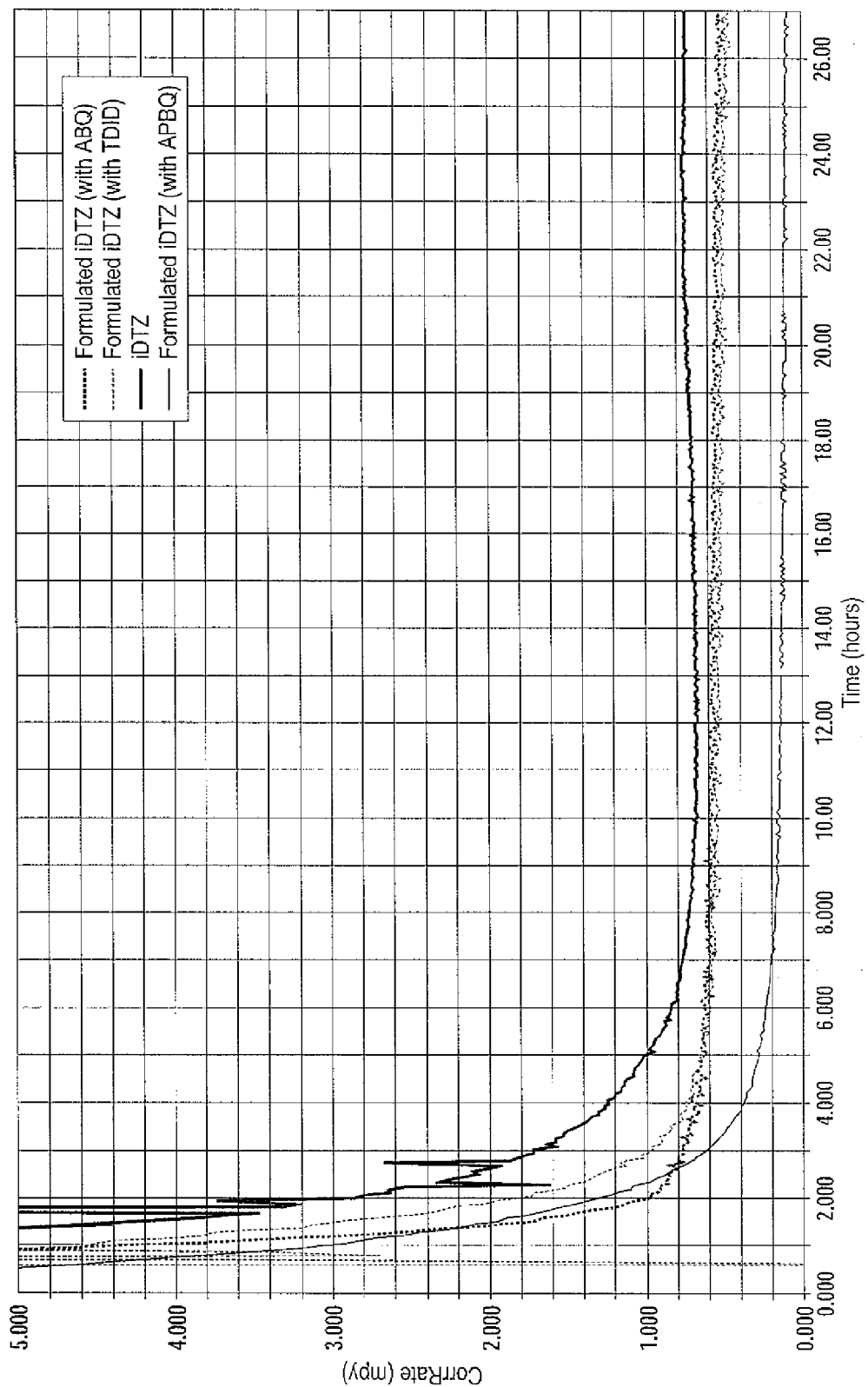
Figure 6:
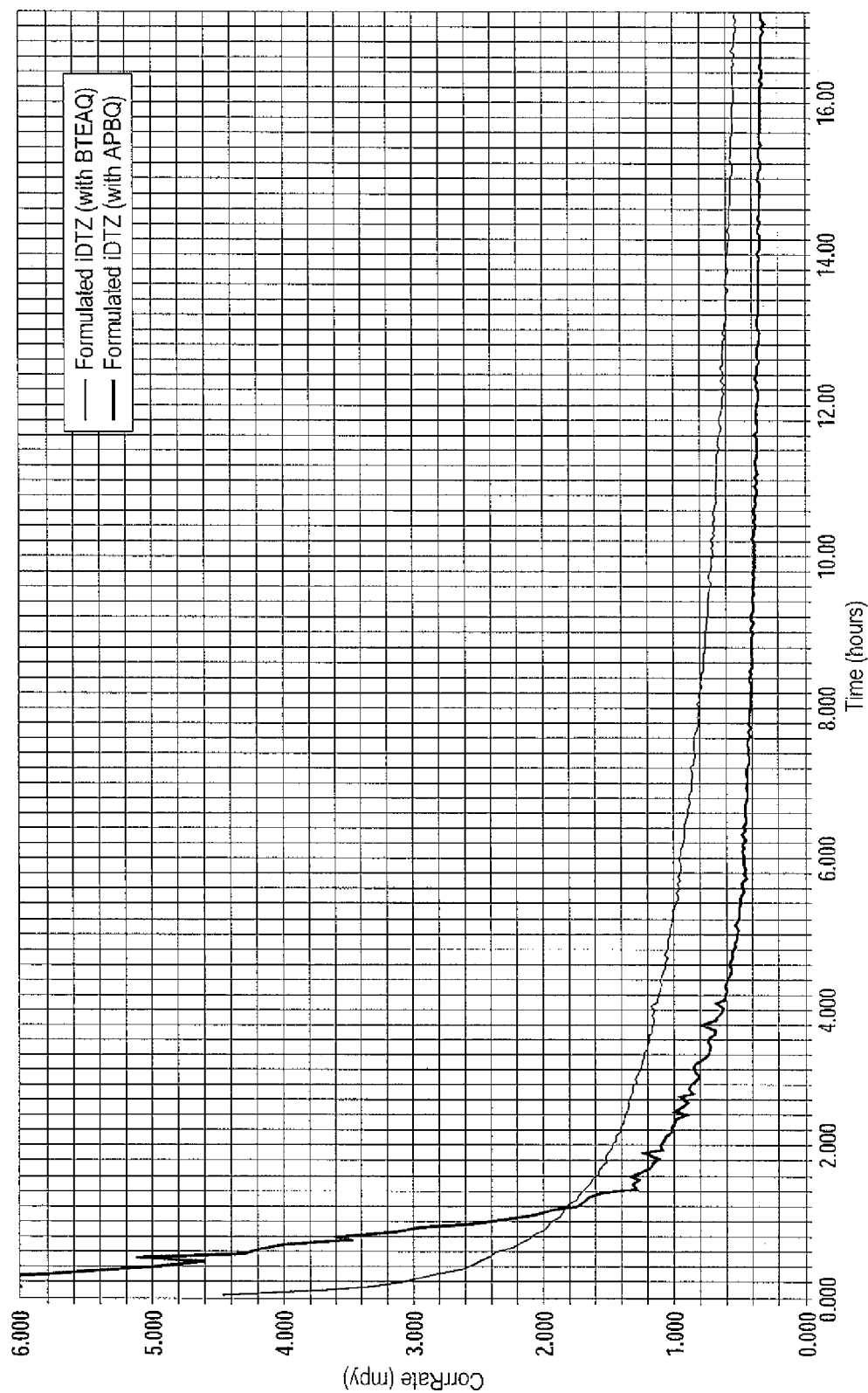
Figure 7:
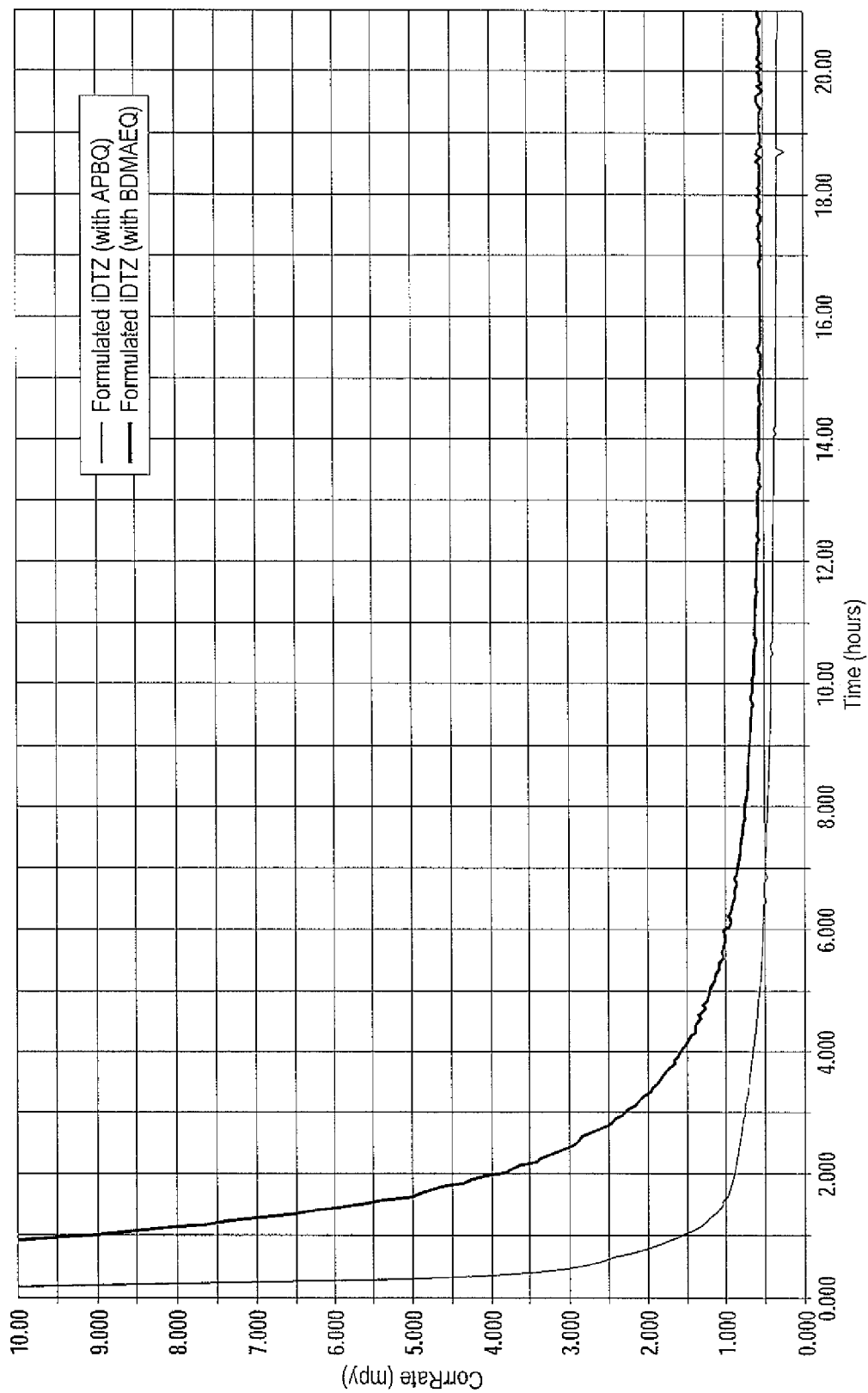

Corrosion rate studies were performed using at ambient temperature a Gamry G Series potentiostat and the conventional Linear Polarization Resistance (LPR) module within the DC 105™ corrosion technique software package (Rp/Ec trend). The instantaneous corrosion rate of the three electrode probe system was determined using voltage settings −0.2V to +0.02V versus open-circuit potential, $E_{oc}$. These studies were carried out during an approximately 20-24 hr run time. The treat rates of the corrosion inhibitors were between 50 and 200 ppm. A standard carbon dioxide saturated brine system comprised of 3 weight percent sodium chloride and 0.3 weight percent calcium chloride in 2 liter corrosion cells sparged with carbon dioxide was employed. LPR scans are shown in FIGS. 1-8 wherein:

FIG. 1 contrasts the differences at a treatment rate of 500 ppm in corrosion rates between WSF and formulated WSF containing the additive APBQ. As shown, much higher corrosion rates are demonstrated with WSF than formulated WSF;

FIG. 2 contrasts the differences at a treatment rate of 500 ppm in corrosion rates between formulated WSF and UF both containing the additive APBQ. As shown, formulated WSF is a better corrosion inhibitor than UF;

FIG. 3 contrasts the differences at a treatment rate of 430 ppm of WFT and iDTZ. FIG. 3 shows that iDTZ is much more effective than WSF as a corrosion inhibitor;

FIG. 4 contrasts the differences at a treatment rate of 430 ppm of Formulated iDTZ (with the additive APBQ) and iDTZ alone. FIG. 4 shows that Formulated iDTZ is a better corrosion inhibitor than iDTZ alone;

FIG. 5 contrasts the differences at a treatment rate of 430 ppm in corrosion rates between iDTZ alone and Formulated iDTZ (with the additive ABQ), Formulated iDTZ (with the additive TDID) and Formulated iDTZ (with the additive APBQ). FIG. 5 shows the Formulated iDTZ (with APBQ) to be the best corrosion inhibitor. Formulated iDTZ (with TDID) and Formulated iDTZ (with ABQ) demonstrate similar results. All of the formulated iDTZs demonstrated better corrosion inhibition than iDTZ alone;

FIG. 6 contrasts the differences at a treatment rate of 125 ppm in corrosion rates between Formulated iDTZ (with BTEAQ) and Formulated iDTZ (with APBQ). FIG. 6 demonstrates better corrosion results with Formulated iDTZ (with APBQ); and FIG. 7 contrasts the differences at a treatment rate of 125 ppm in corrosion rates between Formulated iDTZ (with APBQ) and Formulated iDTZ (with BDMAEQ). FIG. 7 demonstrates better corrosion results with Formulated iDTZ (with APBQ).

Example 2

A dithiazine quaternization reaction product was prepared in accordance with the following synthetic pathway:

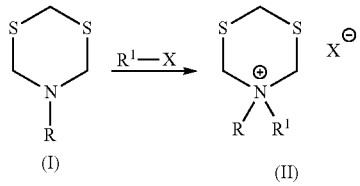

by dissolving in 50 mls of methanol about 2.84 grams (17.2 mmols) of the dithiazine together with a 10% molar excess of the $R^1$-X reagent (2.42 grams, 19.1 mmols). The solution was heated to 125° C. and stirred for 6 hrs in a Parr reactor. Upon cooling the solution was recovered as a dark red.

Figure 8:
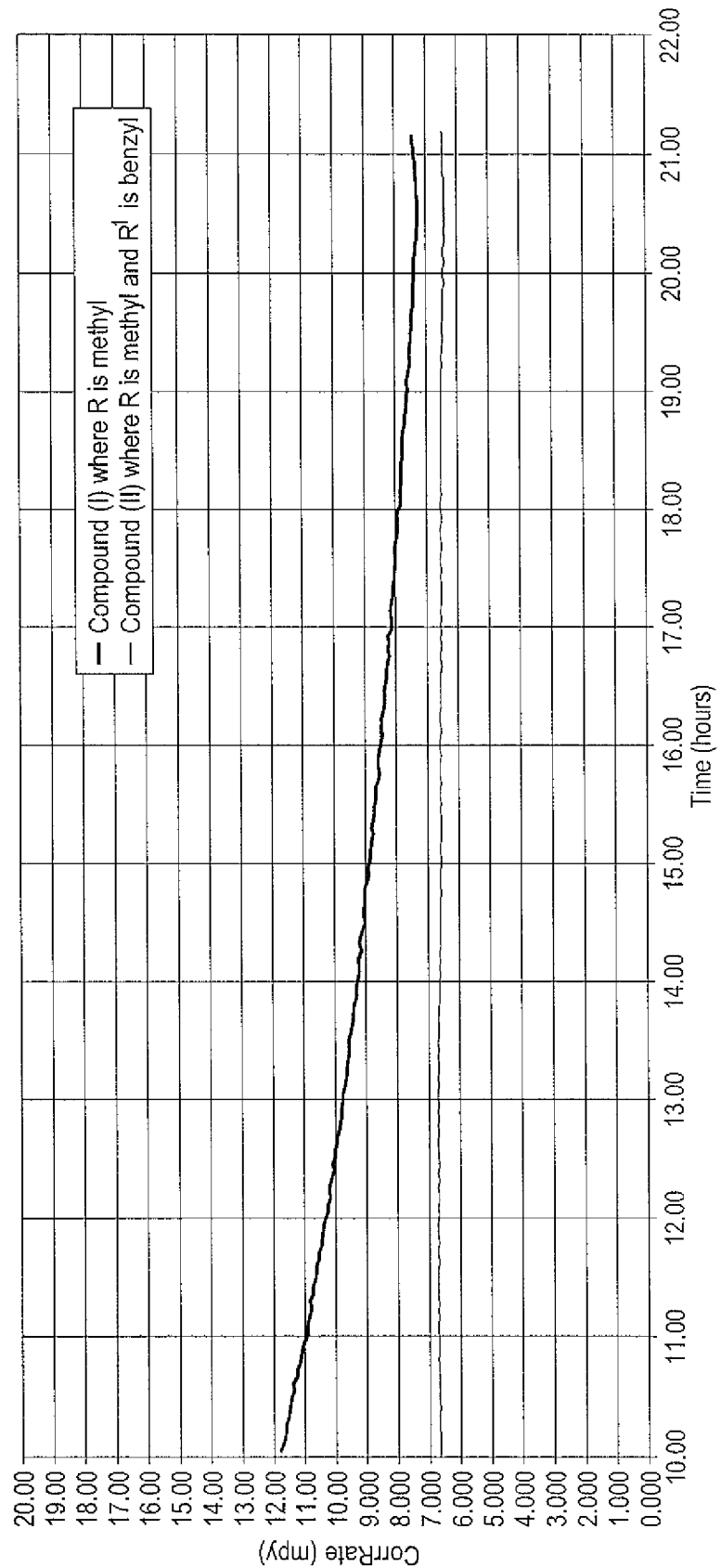
FIGS. 8-12 demonstrate the effectiveness of quaternized reaction products of dithiazine compared to non-quaternized dithiazines.

Corrosion rate studies were conducted using 35 parts of active species per million by mass at ambient temperature on a Gamry G Series potentiostat and the conventional Linear Polarization Resistance (LPR) module within the DC105™ corrosion technique software package (Rp/Ec trend) in accordance with the procedure set forth in Example 1. The instantaneous corrosion rate of the three electrode probe system was determined using voltage settings –0.2V to +0.02V versus open-circuit potential, $E_{oc}$. These studies were carried out during an approximately 20-24 hr run time. The treat rates of the corrosion inhibitors were between 50 and 200 ppm. A standard carbon dioxide saturated brine system comprised of 3 weight percent sodium chloride and 0.3 weight percent calcium chloride in 2 liter corrosion cells sparged with carbon dioxide was employed. LPR scans are shown in FIGS. 8-10 wherein:

FIG. 8 contrasts the differences of compound (I) wherein R is methyl at 35 parts per million (ppm) (by mass) [or 0.26 ppm (by moles)] and compound (II) wherein R is methyl and $R^1$ is benzyl at 35 parts per million (ppm) (by mass) [or 0.13 ppm (by moles)].

Figure 9:
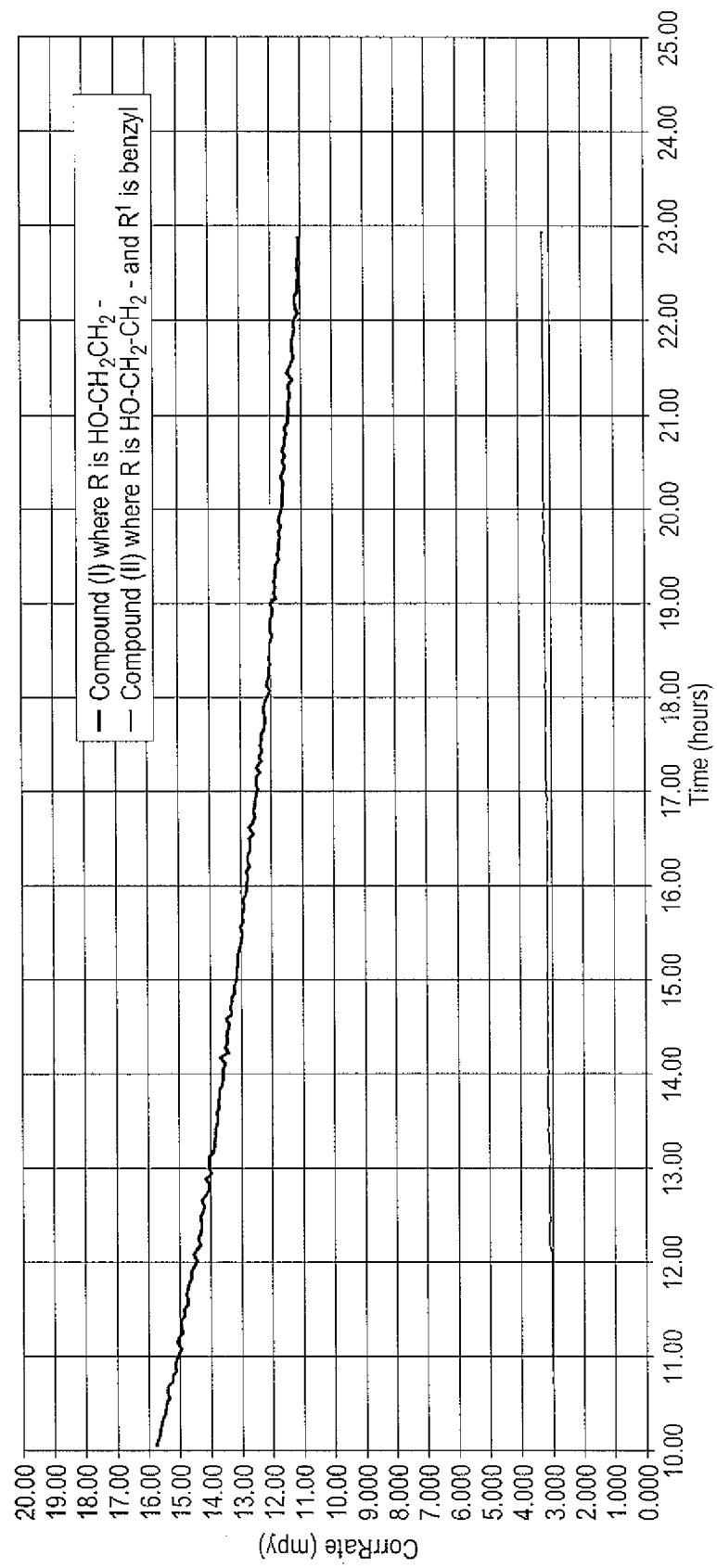

FIG. 9 contrasts the differences of compound (I) wherein R is HO—$CH_2$—$CH_2$—35 parts per million (ppm) (by mass) [or 0.21 ppm (by moles)] and compound (II) wherein R is HO—$CH_2$—$CH_2$— and $R^1$ is benzyl at 35 parts per million (ppm) (by mass) [or 0.12 ppm (by moles)].

Figure 10:
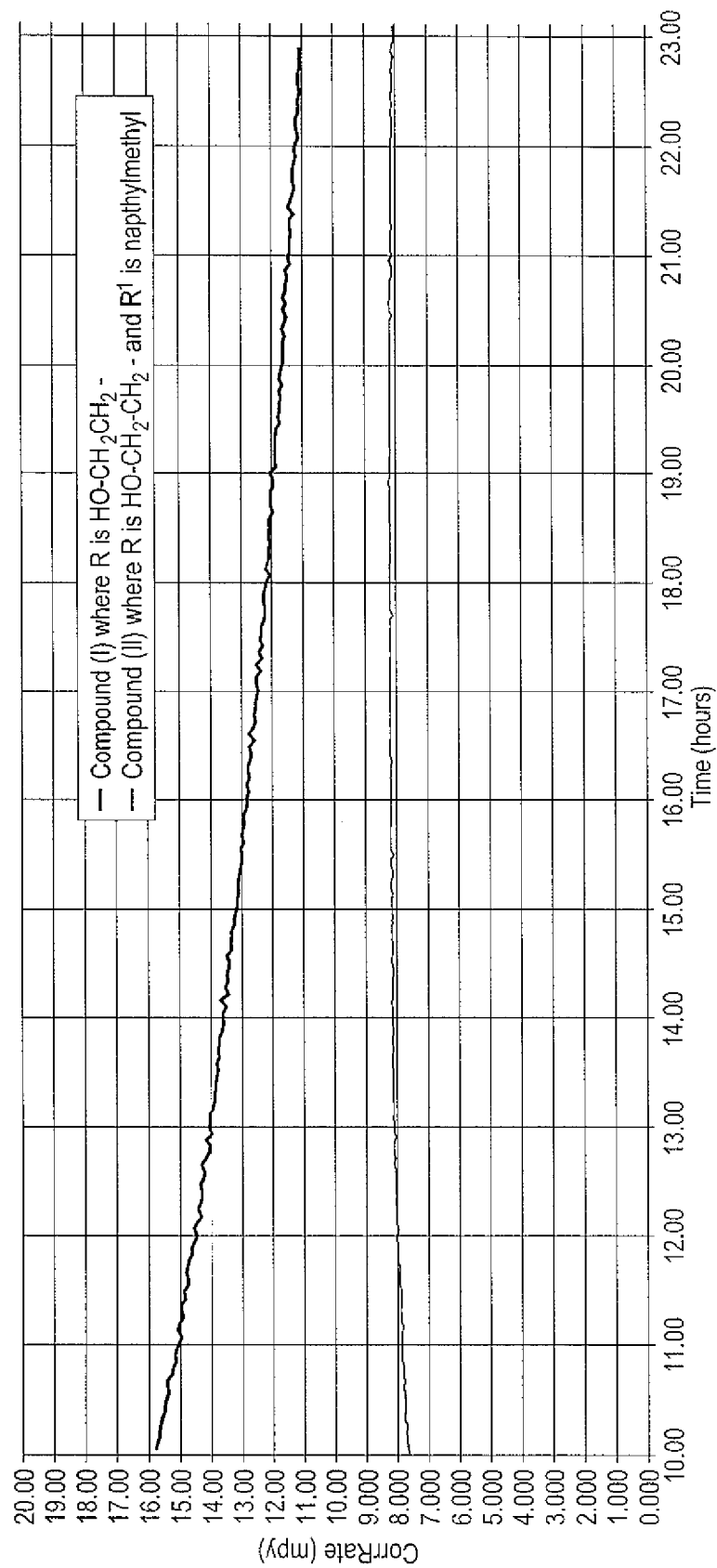

FIG. 10 contrasts the differences of compound (I) wherein R is HO—$CH_2$—$CH_2$—at 35 ppm [or 0.21 ppm (by moles)] and compound (B) wherein R is HO—$CH_2$—$CH_2$— and $R^1$ is naphthylmethyl at 35 parts per million (ppm) (by mass) [or 0.10 ppm (by moles)].

As shown, much better corrosion rate inhibition is demonstrated with the derivatized dithiazines represented by compound (II) than compound (I) especially considering that lower molar quantities of the derivatized dithiazines were used.

Example 3

A dithiazine quaternization reaction product was prepared in accordance with the following synthetic pathway:

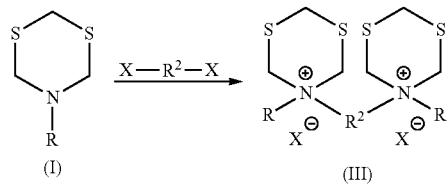

by dissolving in 50 mls of methanol about 3 grams (18.2 mmols) of the dithiazine together with the X-$R^2$-X- reagent (9.1 mmols). The solution was heated to 125° C. and stirred for 6 hrs in a Parr reactor. Upon cooling the solution was recovered as a dark red.

Figure 11:
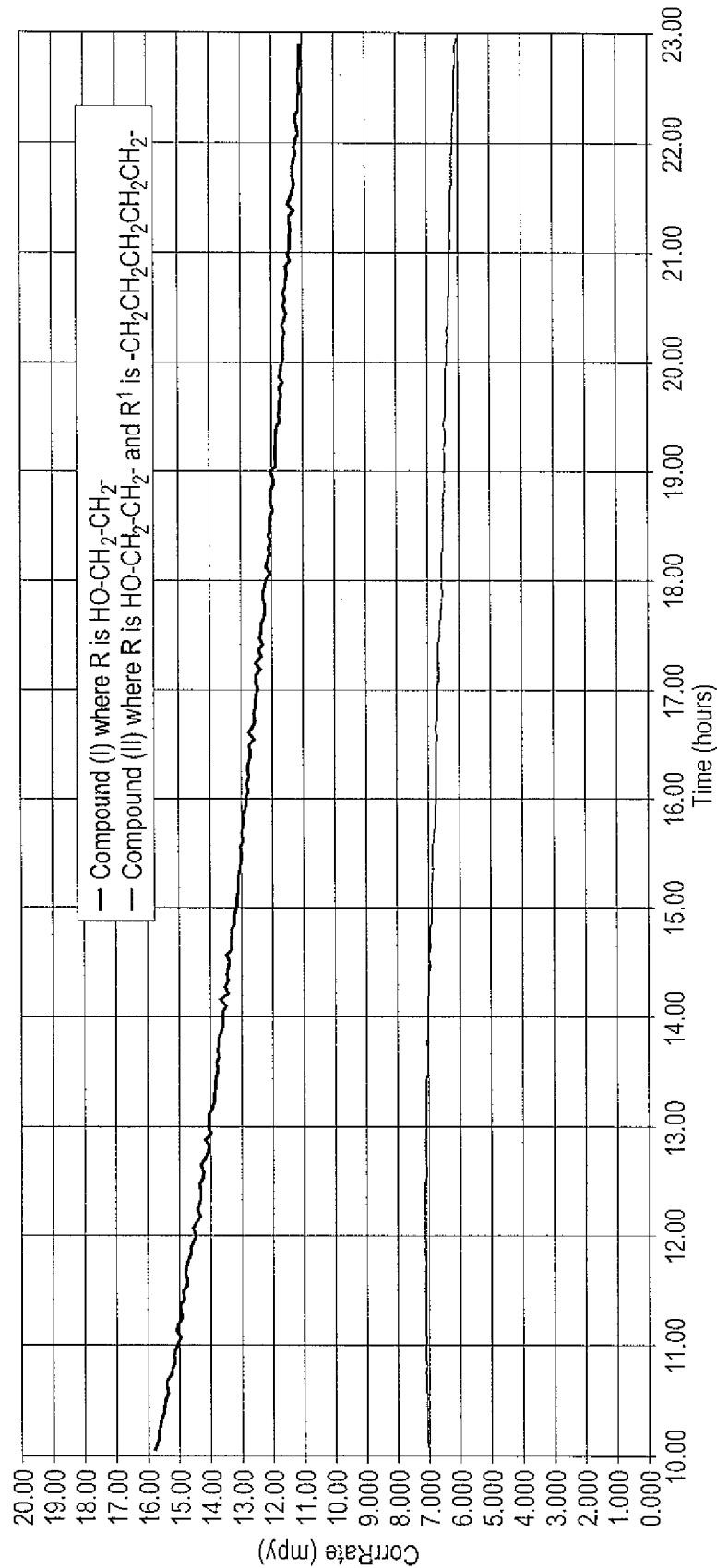

Corrosion rate studies were conducted at ambient temperature on a Gamry G Series potentiostat and the conventional Linear Polarization Resistance (LPR) module within the DC105™ corrosion technique software package (Rp/Ec trend) in accordance with the procedure set forth in Example 1. The instantaneous corrosion rate of the three electrode probe system was determined using voltage settings –0.2V to +0.02V versus open-circuit potential, $E_{oc}$. These studies were carried out during an approximately 20-24 hr run time. The treat rates of the corrosion inhibitors were between 50 and 200 ppm. A standard carbon dioxide saturated brine system comprised of 3 weight percent sodium chloride and 0.3 weight percent calcium chloride in 2 liter corrosion cells sparged with carbon dioxide was employed. LPR scans are shown in FIGS. 11 and 12 wherein:

FIG. 11 contrasts the differences of the structure of formula (I) wherein R is HO—$CH_2$—$CH_2$—at 0.21 ppm (by moles) and the structure of formula (II) wherein R is HO—$CH_2$—$CH_2$— and $R^3$ is $C_5H_1$ at 0.12 ppm (by moles).

Figure 12:
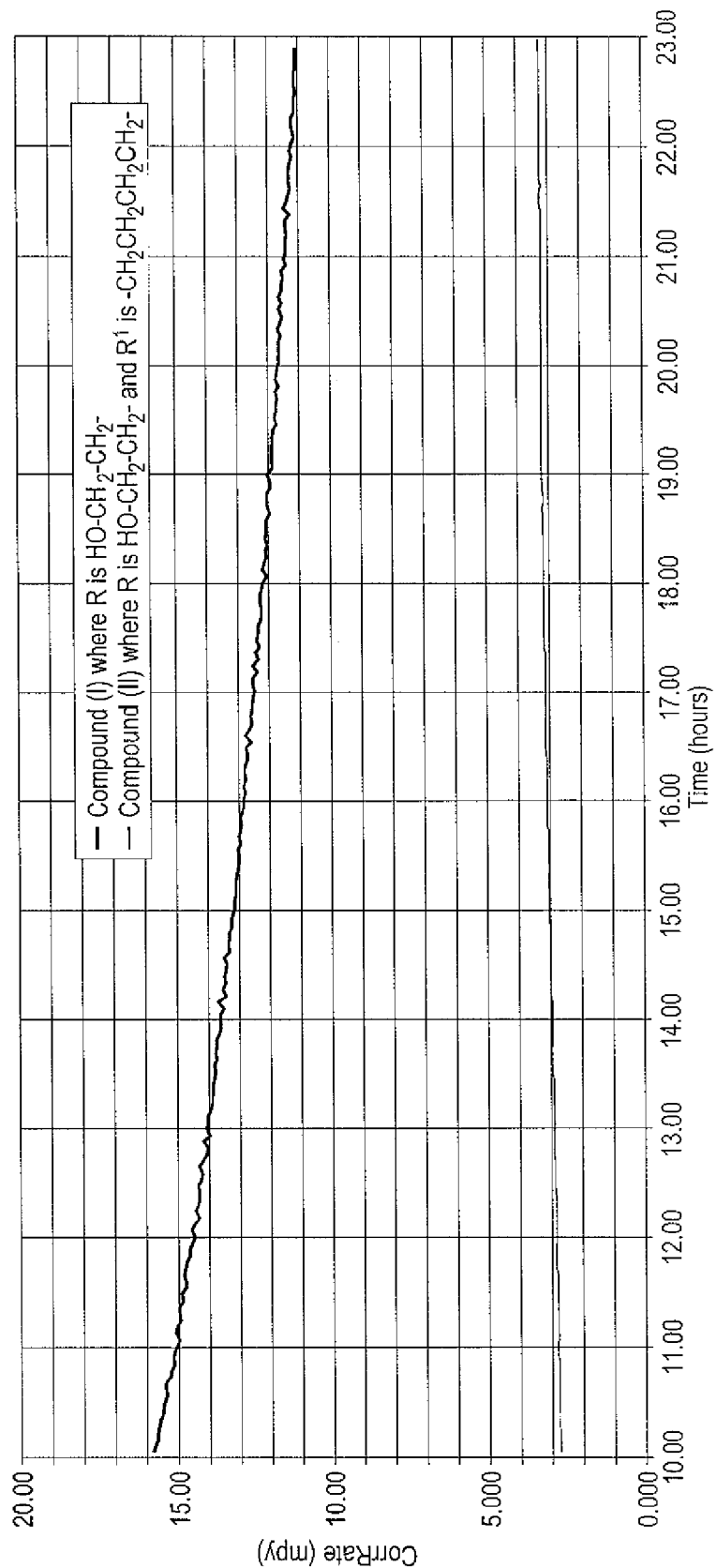

FIG. 12 contrasts the differences of the structure of formula (I) wherein R is HO—$CH_2$—$CH_2$—at 0.21 ppm (by moles) and the structure of formula II) wherein R is HO—$CH_2$—$CH_2$—and $R^3$ is $C_4H_9$ at 0.12 ppm (by moles).

As shown, much better corrosion rate inhibition is demonstrated with the derivatized dithiazines represented by compound (II) than the dithiazines represented by compound (I).

From the foregoing, it will be observed that numerous variations and modifications may be effected without departing from the true spirit and scope of the novel concepts of the invention.

What is claimed is:

1. A quaternized dithiazine of the formula:

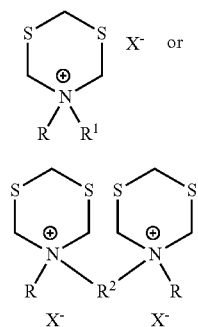

wherein:
R is —CH$_3$ or —CH$_2$CH$_2$OH,
R$^1$ is benzyl or naphthylmethyl;
R$^2$ is —CH$_2$—CH$_2$—CH$_2$—CH$_2$— or —CH$_2$—CH$_2$—CH$_2$—CH$_2$—CH$_2$—; and
X is —Cl, —Br or —I.

2. The quaternized dithiazine of claim 1 wherein X is —Cl.

3. The quaternized dithiazine of claim 2 having the structural formula (A) wherein R is —CH$_2$CH$_2$OH and R$^1$ is naphthylmethyl.

4. The quaternized dithiazine of claim 2 having the structural formula (A) wherein R is CH$_3$ and R$^1$ is naphthylmethyl.

5. The quaternized dithiazine of claim 2 having the structural formula (A) wherein R is —CH$_2$CH$_2$OH and R$^1$ is benzyl.

6. The quaternized dithiazine of claim 2, having the structural formula (A) wherein R is —CH$_3$ and R$^1$ is benzyl.

7. The quaternized dithiazine of claim 2 having the structural formula (B) wherein R is HO—CH$_2$—CH$_2$— and R$^2$ is selected from the group consisting of —CH$_2$—CH$_2$—CH$_2$—CH$_2$— and —CH$_2$—CH$_2$—CH$_2$—CH$_2$—CH$_2$—.

8. A method of inhibiting corrosion of iron and ferrous base materials during the treatment of a subterranean formation which comprises introducing into a gas or oil well a corrosive inhibiting effective amount of a quaternized dithiazine of the formula:

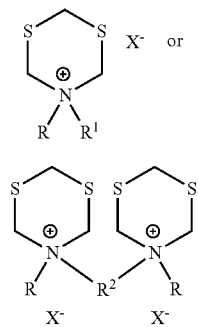

wherein:
R is selected from the group consisting of a C$_1$ to C$_{12}$ saturated or unsaturated hydrocarbyl group or a C$_1$ to C$_{10}$ ω-hydroxy saturated or unsaturated hydrocarbyl group;
R$^1$ is selected from the group consisting of a C$_1$-C$_{24}$ straight chain or branched alkyl group or a C$_1$-C$_{24}$ arylalkyl group; and
R$^2$ is a straight or branched chain C$_1$-C$_6$ alkylene group; and
each X is chlorine, bromine or iodine
for a time sufficient to inhibit corrosion of the iron and ferrous base materials.

9. The method of claim 8, which further comprises introducing into the well, with the quaternized dithiazine at least one component selected from the group consisting of:
(a) an alkyl, hydroxyalkyl, alkylaryl arylalkyl or arylamine quaternary salt;
(b) a mono or polycyclic aromatic amine salt;
(c) an imidazoline derivative;
(d) a mono-, di- or trialkyl or alkylaryl or arylalkyl phosphate ester; and
(e) a monomeric or oligomeric fatty acid.

10. The method of claim 9, wherein the at least one component is an alkyl, hydroxyalkyl, alkylaryl arylalkyl or arylamine quaternary salt.

11. The method of claim 10, wherein the quaternary salt of the at least one component is of the formula [N$^+$R$^5$R$^6$R$^7$R$^8$][X$^-$] wherein each of R$^5$, R$^6$, R$^7$ and R$^8$ contain 1 to about 18 carbon atoms and X is Cl, Br or I.

12. The method of claim 11, wherein at least one of R$^5$, R$^6$, R$^7$ and R$^8$ is a C$_1$-C$_6$ alkyl group or a hydroxyalkyl group wherein the alkyl group is a C$_1$-C$_6$ alkyl or an alkyl aryl or arylalkyl.

13. The method of claim 8, wherein the quaternized dithiazine is of the structure (A) wherein R is —R$^3$—OH and further wherein R$^3$ is an alkylene group.

14. The method of claim 13, wherein R is a C$_1$-C$_6$—OH group.

15. The method of claim 14, wherein R is —CH$_2$CH$_2$—OH.

16. The method of claim 8, wherein the quaternized dithiazine is of the structure (A) wherein R is —CH$_2$CH$_2$—OH or —CH$_3$ and R$^1$ is either 1-naphthyl methylene or benzyl.

17. The method of claim 16, wherein the quaternized dithiazine is of the formula:

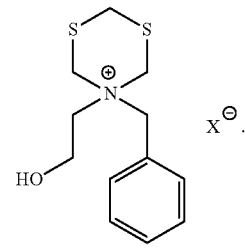

18. The method of claim 17, wherein X is chlorine.

19. The method of claim 16, wherein the quaternized dithiazine is of the formula:

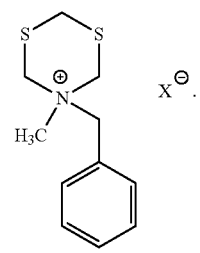

20. The method of claim 19, wherein X is chlorine.

21. The method of claim 16, wherein the quaternized dithiazine is of the formula:

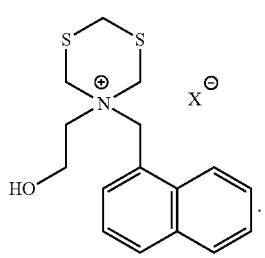

22. The method of claim 21, wherein X is chlorine.

23. The method of claim 16, wherein the quaternized dithiazine is of the formula:

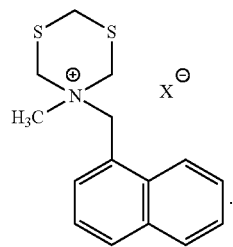

24. The method of claim 23, wherein X is chlorine.

25. The method of claim 8, wherein the quaternized dithiazine is prepared by reacting a dithiazine of the formula:

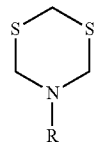

with either a compound of the formula $R^1X$ or $X-R^4-X$ wherein $R^4$ is a $C_1$-$C_6$ alkylene group.

26. The method of claim 25, wherein the dithiazine is isolated from a spent fluid formed by reaction of hydrogen sulfide and a triazine of the formula:

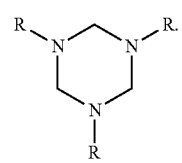

(II)

27. The method of claim 25, wherein the dithiazine is a component of the spent fluid formed by reaction of hydrogen sulfide and a triazine of the formula:

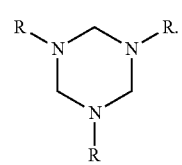

(II)

28. The method of claim 8, wherein the quaternized dithiazine is of the structure (A) wherein $R^1$ is a straight chain or branched $C_1$-$C_{12}$ alkyl group.

29. The method of claim 8, wherein the quaternized dithiazine is of the structure (A) wherein $R^1$ is a straight chain or branched $C_1$-$C_6$ alkyl group.

30. The method of claim 8, wherein the quaternized dithiazine is of the structure (B) wherein R is —$CH_3$ or —$CH_2CH_2OH$ and $R^2$ is —$CH_2$—$CH_2$—$CH_2$—$CH_2$—$CH_2$— or —$CH_2$—$CH_2$—$CH_2$—$CH_2$—$CH_2$—$CH_2$—.

31. The method of claim 8, wherein the quaternized dithiazine is introduced into the well during stimulation.

32. The method of claim 8, whereby the corrosive effect of an acid solution on metal contacted by an aqueous acid solution is minimized by the addition of the quaternized dithiazine to the well.

* * * * *